United States Patent
Berti et al.

(10) Patent No.: US 6,476,611 B2
(45) Date of Patent: Nov. 5, 2002

(54) CIRCUIT AND A METHOD FOR MONITORING AND DIAGNOSING AN OXYGEN PROBE

(75) Inventors: Marco Berti, Turin (IT); Piero Carbonaro, Turin (IT); Daniele Ceccarini, Rimini (IT); Luca Poggio, Spinetta Marengo (IT)

(73) Assignee: Magnetic Marelli S.p.A. (IT)

( * ) Notice: Subject to any disclaimer, the term of this patent is extended or adjusted under 35 U.S.C. 154(b) by 0 days.

(21) Appl. No.: 09/804,057

(22) Filed: Mar. 13, 2001

(65) Prior Publication Data

US 2002/0008524 A1 Jan. 24, 2002

(30) Foreign Application Priority Data

Mar. 15, 2000 (IT) .......................... BO00A0143

(51) Int. Cl.[7] ................................ F02P 17/00
(52) U.S. Cl. ....................... 324/379; 73/25.01
(58) Field of Search ................ 324/379, 713; 73/25.01, 117.3; 204/42.5

(56) References Cited

U.S. PATENT DOCUMENTS

| 4,819,602 A | 4/1989 | Mieno et al. |
| 4,905,652 A | 3/1990 | Nakajima et al. |
| 5,219,228 A | * 6/1993 | Ker ............................ 324/713 |
| 2001/0020587 A1 | 9/2001 | Amtmann et al. |

FOREIGN PATENT DOCUMENTS

| DE | 19836128 | 2/2000 |

OTHER PUBLICATIONS

European Search Report EP 01106273.

* cited by examiner

Primary Examiner—Christine K. Oda
(74) Attorney, Agent, or Firm—Hall, Priddy, Myers & Vande Sande

(57) ABSTRACT

A circuit for monitoring and diagnosing an oxygen probe provided with a sensitive cell connected between a first and a second signal terminal, and a heating member connected between a battery and a heating terminal; the circuit includes an interface stage and a control unit. The interface stage includes a first resistor connected between a switch which is normally open and a supply line at a known potential and the first signal terminal, a second resistor connected between the first signal terminal and a second signal terminal and a third resistor connected between the second signal terminal and reference potential line. The control unit further includes a first analog-digital converter connected to the first signal terminal and a second analog-digital converter connected to the second signal terminal.

11 Claims, 2 Drawing Sheets

CIRCUIT AND A METHOD FOR MONITORING AND DIAGNOSING AN OXYGEN PROBE

The present invention relates to a circuit and a method for monitoring and diagnosing an oxygen probe.

BACKGROUND OF THE INVENTION

As is known, internal combustion engines are provided with systems for exhaust gas reduction, based on the information provided by oxygen probes (the so-called LAMBDA probes), and electronic control units whose tasks include, among other things, minimising emissions of pollutant substances and verifying, with the assistance of appropriate circuits, the correct operation of the various components, in particular the oxygen probes. These probes normally comprise a sensitive cell having an internal resistance and providing a voltage signal whose amplitude varies as a function of the oxygen concentration present in the atmosphere in which the sensitive cell is immersed, and a heating member, for instance formed by a resistor, which makes it possible to maintain the temperature of the sensitive cell within a predetermined range of operating values, for instance between approximately 600° C. and approximately 800° C.

Various types of circuits and relative methods for monitoring and diagnosing oxygen probes are known.

According to a first solution, a resistor having a known resistance value is disposed in series with the heating member, while a differential amplifier detects the voltage drop at the resistor and supplies a control unit of the electronic control unit with an output signal representative of this voltage drop. According to the solution described above, the output signal of the differential amplifier is digitised and is used to calculate, in a manner known per se, the current flowing in the resistor and in the heating member and to regulate, for instance by means of a controller of proportional-integral type, the power dissipated by the latter. The control unit, verifies, moreover, whether the current is maintained within a predetermined range of operating values. If not, a malfunction of the heating member is detected.

A second solution entails the use of a differential amplifier having inputs connected to the terminals of the sensitive cells and an output connected to the control unit. In this case, a current is injected into the probe in order to estimate its internal resistance which is linked to the temperature of the probe according to a known relationship. The temperature of the probe may be adjusted again using a controller of proportional-integral type.

Although the solutions described above are accurate and reliable, they nevertheless entail drawbacks as they make use of costly circuits, in particular as a result of the differential amplifier and, in the first case, also of the shunt resistor.

SUMMARY OF THE INVENTION

The object of the present invention is to provide a circuit for monitoring and diagnosing an oxygen probe which is simple and economic to construct.

The present invention therefore relates to a circuit for monitoring and diagnosing an oxygen probe, provided with a sensitive cell, connected between a first and a second signal terminal, and a heating member, connected between a battery and a heating terminal, the circuit comprising an interface stage and a control unit, this interface stage comprising a first resistor connected between a supply line and the first signal terminal of the oxygen probe, a second resistor connected between the first signal terminal and the second signal terminal of the oxygen probe, the circuit being characterised in that the control unit comprises first analog-digital converter means connected to the first signal terminal, and a second analog-digital converter means connected to the second signal terminal, and in that the interface stage comprises a third resistor connected between the second signal terminal and a reference potential line.

The present invention also relates to a method for monitoring and diagnosing an oxygen probe, as defined in claim 5.

BRIEF DESCRIPTION OF THE DRAWINGS

The invention is described in further detail below with reference to a preferred embodiment thereof, giving purely by way of non-limiting example, and made with reference to the accompanying drawings, in which.

DETAILED DESCRIPTION OF THE INVENTION

Figure 1:
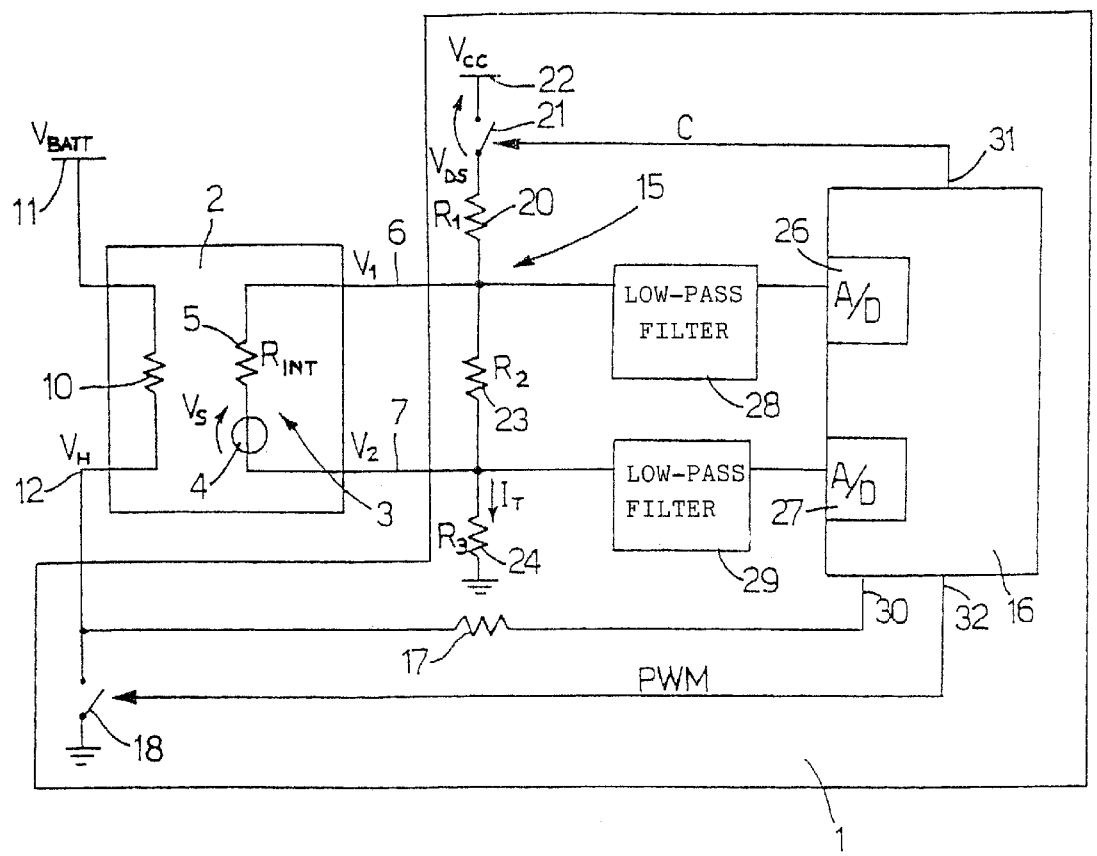
FIG. 1 is a simplified electrical diagram of a monitoring and diagnosis circuit of the present invention.

In FIG. 1, a circuit for monitoring and diagnosing an oxygen probe 2 is indicated by reference numeral 1.

This oxygen probe 2 comprises a sensitive cell 3, shown by means of a voltage generator 4, supplying a probe voltage $V_s$, and an internal resistor 5, having an internal resistance value $R_{INT}$, connected together in series and disposed between a first and a second signal terminal 6, 7, respectively having a first and a second signal voltage $V_1$, $V_2$, and a heating member 10, shown by a resistor connected between a battery 11, supplying a battery voltage $V_{BATT}$, and a heating terminal 12 of the oxygen probe 2. The difference between the first and the second signal voltage $V_1$, $V_2$, moreover, represents an output voltage $V_o$ of the oxygen probe 2.

The monitoring and diagnosis circuit 1 comprises an interface stage 15, a control unit 16, a diagnosis resistor 17 and a drive switch 18, formed for instance by a transistor of MOS type, disposed between the heating terminal of the oxygen probe 2 and earth.

The interface stage 15 comprises a first resistor 20 having a first terminal connected to the first signal terminal 6 of the oxygen probe 2 and a second terminal connected, via an interface switch 21 which is normally open (for instance a transistor of MOS type), to a supply line 22 supplying a supply voltage $V_{CC}$, a second resistor 23 connected between the first and the second signal terminals 6, 7, and a third resistor 24 disposed between the second signal terminal 7 and earth. The first, the second and the third resistor 20, 23, 24 moreover have respective first, second and third resistance values $R_1$, $R_2$, $R_3$.

The control unit 16, formed by a microprocessor of a type known per se, comprises a first and a second analog-digital converter 26, 27 respectively connected to the first and the second signal terminals 6, 7 of the oxygen probe 2 via low-pass filters 28, 29 (for instance RC filters of the first order).

The control unit 16, moreover, has a diagnosis input 30, connected to the heating terminal 12 of the oxygen probe 2 via the diagnosis resistor 17, a control output 31 and a drive output 32.

In further detail, the control output 31 is connected to a control terminal of the interface switch 21 and supplies a control signal C, having a first and a second logic value, in correspondence with which the interface switch 21 is controlled to open and respectively to close.

The drive output 32 is connected to a control terminal of the drive switch 18 and supplies a drive signal PWM of a square wave type with a variable duty-cycle, in order alternatively to control the opening and closing of the drive switch 18 depending on the amplitude of this duty-cycle.

The monitoring and diagnosis circuit 1 makes it possible to measure the internal resistance value $R_{INT}$ of the sensitive cell 3 in the manner described below with reference to FIG. 2.

The control signal C is normally maintained at the first logic value, in order to keep the interface switch 21 open (block 100).

The current values of the first and second signal voltage $V_1$, $V_2$, indicated respectively as $V_{1OFF}$ and $V_{2OFF}$ are initially acquired (block 110), and an initial output voltage $V_{\lambda 1}$ of the output voltage $V_O$ is calculated (block 120) on the basis of the equation:

$$V_{\lambda 1} = V_{1OFF} - V_{2OFF} \tag{1}$$

Immediately after the acquisition of the current values $V_{1OFF}$ and $V_{2OFF}$, the control signal C is set to the second logic value (block 130), in order to control the closure of the interface switch 21 and to inject a test current $I_T$ (FIG. 1) and the current values of the first and second signal voltage $V_1$, $V_2$, indicated respectively as $V_{1ON}$ and $V_{2ON}$, are acquired for a second time (block 140).

Once these values have been acquired, the control signal C is again set to the first logic value in order to re-open the interface switch 21 and reset the normal operating conditions of the monitoring and diagnosis circuit 1 and of the oxygen probe 2 (block 145).

Thereafter, a second output value $V_{\lambda 2}$ of the output voltage $V_O$ (block 150) and the value of the test current $I_T$ (block 160) are calculated on the basis of the equations:

$$V_{\lambda 2} = V_{1ON} - V_{2ON} \tag{2}$$

and respectively $$I_T = V_{2ON}/R_3 \tag{3}$$

If, as a result of a malfunction, there is a dispersion between the second signal terminal 7 and earth, the second signal voltage $V_2$ remains close to a zero value irrespective of the state of the interface switch 21. In this case the following equation is used in place of equation (3) for the calculation of the test current $I_T$:

$$I_T = \frac{V_{CC} - V_{1ON} - V_{DS}}{R_1} \tag{3'}$$

where $V_{DS}$ is the voltage drop at the terminals of the interface switch 21 when it is closed. This voltage drop may be considered constant and is known.

The internal resistance value $R_{INT}$ is lastly calculated (block 170) according to the equation:

$$R_{INT} = \frac{R_2(V_{\lambda 2} - V_{\lambda 1})}{R_2 I_T - (V_{\lambda 2} - V_{\lambda 1})} \tag{4}$$

Equation (4) may be obtained in the following way. The first output value $V_{\lambda 1}$ which is obtained when the interface switch 21 is open is given by the relationship:

$$V_{\lambda 1} = \frac{R_2}{R_{INT} + R_2} V_s \tag{5}$$

When the interface switch 21 is closed, the output voltage $V_O$ of the oxygen probe 2 assumes the second output value $V_{\lambda 2}$ given by the expression:

$$V_{\lambda 2} = \frac{R_2}{R_{INT} + R_2} V_S + R_P I_T \tag{6}$$

where $R_P$ is the resistance value of the parallel between the internal resistor 5 and the second resistor 23 (FIG. 1) and can be obtained from the well-known relationship:

$$R_P = \frac{R_{INT} R_2}{R_{INT} + R_2} \tag{7}$$

Given that the value of the probe voltage $V_S$ does not vary in both cases, equations (5) and (6) can be combined to given the expression:

$$V_{\lambda 2} = V_{\lambda 1} + R_P I_T \tag{8}$$

from which the following equation is obtained $$R_P = \frac{V_{\lambda 2} - V_{\lambda 1}}{I_T} \tag{9}$$

Equation (4) can be readily obtained by equating the second members of equation (7) and (9) and making the internal resistance value $R_{INT}$ explicit.

Figure 3:
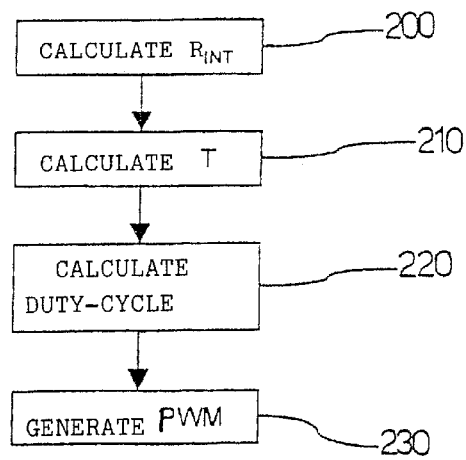
FIGS. 2 and 3 are flow diagrams relating to a monitoring and diagnosis method of the present invention.

As shown in FIG. 3, a method for monitoring the oxygen probe 2, in particular the temperature T of the sensitive cell 3, involves the initial calculation of the internal resistance value $R_{INT}$ of the sensitive cell 3 by means of the procedure described with reference to FIG. 2 (block 200).

A current value of the temperature T of the sensitive cell 3 is then calculated by means of the (known) reaction that links the temperature T to the internal resistance value $R_{INT}$ (block 210).

Thereafter, by means of a control function of a known type (for instance a control function of a proportional-integral type), the duty-cycle that needs to be provided for the drive signal PWM in order to supply the heating member 10 with the electrical power needed to maintain the sensitive cell 3 at the desired temperature is calculated (block 220).

Lastly, the drive signal PWM, having the previously predetermined duty-cycle, is supplied to the control terminal of the drive switch 18 in order to control the power dissipated by the heating member 10 (block 230).

The monitoring and diagnosis circuit 1 makes it possible, moreover, to carry out procedures to diagnose any malfunctions of the sensitive cell 3 and the heating member 10.

Figure 2:
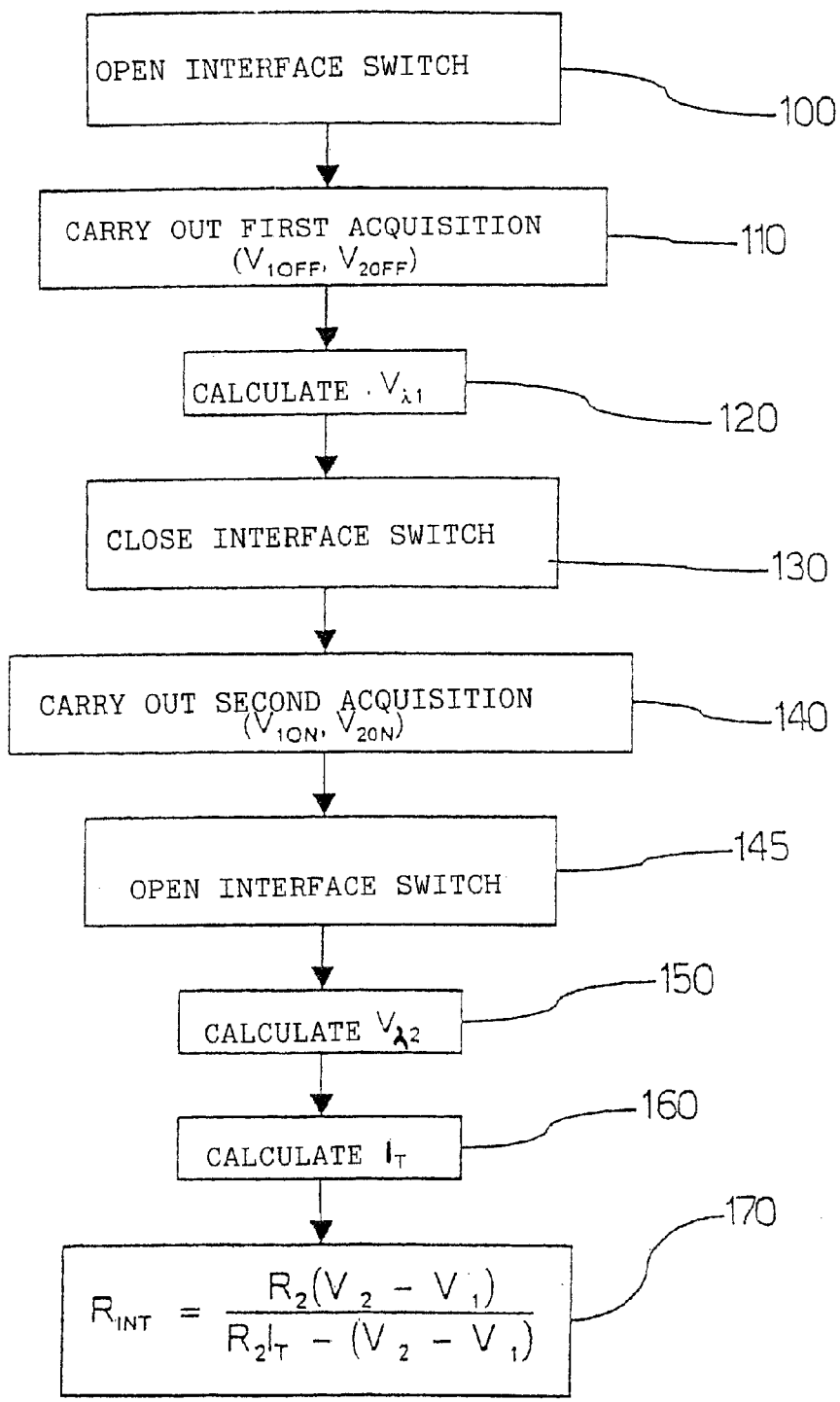

As regards the sensitive cell 3, the current values $V_{1ON}$ and $V_{2ON}$ of the first and second signal voltages $V_1$, $V_2$ acquired during the calculation of the internal resistance value $R_{INT}$ after the closure of the interface switch 21, are used (blocks 130 and 140 of FIG. 2). In particular, if the current value $V_{1ON}$ of the first signal voltage $V_1$ is greater than a predetermined upper threshold, the presence of a dispersion between the first signal terminal 6 and the supply line 22 is detected and signalled. If the current value $V_{2ON}$ of the second signal voltage $V_2$ is lower than a predetermined lower threshold, the existence of a dispersion between the second signal terminal 7 and earth is diagnosed. In this case, moreover, a state bit is updated to indicate that equation (3') should be used in place of equation (3) for the calculation of the internal resistance value $R_{INT}$ of the sensitive cell 3.

The operational nature of the heating member 10 is evaluated by detecting, by means of the diagnosis resistor 17 and the diagnosis input 30 of the control unit 16, a heating voltage $V_H$ present at the heating terminal 12 of the oxygen probe 2 (FIG. 1) and comparing it with a predetermined reference voltage. In detail, if the heating voltage $V_H$ is greater than the predetermined reference voltage even when the drive switch 18 is closed, a malfunction due to a dispersion between the heating terminal 12 and the battery 11 is signalled. If, however, the heating voltage $V_H$ is smaller than the predetermined reference voltage, even when the drive switch 18 is open, a dispersion between the heating terminal 12 and earth is signalled.

It is possible, moreover, to diagnose a reduction of the efficiency of the heating member 10 by calculating the internal resistance value $R_{INT}$ which decreases as the temperature T of the sensitive cell 3 increases. For this purpose, it is verified whether this internal resistance value $R_{INT}$ continues to remain above a threshold resistance value even with a 100% duty-cycle of the drive signal PWM. If so, a malfunction is signalled since, even when the maximum power is supplied, the heating member 10 is no longer able to maintain the temperature T of the sensitive cell 3 at acceptable values.

The advantages of the monitoring and diagnosis circuit of the invention are clearly evident from the above description.

In the first place, the differential amplifier contained in known devices is omitted, providing a substantial cost advantage.

The monitoring and diagnosis circuit 1 is also very accurate and robust. The possibility of calculating the test current $I_T$ that is injected makes the measurement of the internal resistance value $R_{INT}$ of the sensitive cell 3 accurate and reliable. Moreover, even in the case of partial malfunction of the circuit, it is possible to use an alternative method for the calculation of the test current $I_I$ using equation (3') It will be appreciated that modifications and variations may be made to the method described above provided that they do not depart from the scope of protection of the present invention.

What is claimed is:

1. A circuit for monitoring and diagnosing an oxygen probe (2) provided with a sensitive cell (3) connected between a first and a second signal terminal (6, 7) and a heating member (10) connected between a battery (11) and a heating terminal (12), the circuit comprising an interface stage (15) and a control unit (16), the interface stage (15) comprising a first resistor (20) connected between a supply line (22) and the first signal terminal (6) of the oxygen probe (2), and a second resistor (23) connected between the first signal terminal (6) and the second signal terminal (7) of the oxygen probe (2), the circuit being characterized in that the control unit (16) comprises first analog-digital converter means (26) connected to the first signal terminal (6), and the second analog-digital converter means (27) connected to the second signal terminal (7) and in that the interface stage (15) comprises a third resistor (24) connected between the second signal terminal (7) and a reference potential line.

2. A circuit as claimed in claim 1, characterised in that the interface stage (15) comprises interface switch means (21) connected between the first resistor (20) and the supply line (22) and having a control terminal connected to a control output (31) of the control unit (16), the control output (31) supplying a control logic signal (C) in order alternatively to command the opening and closing of the interface switch means (21).

3. A circuit as claimed in claim 1, characterised in that the control unit (16) has a diagnosis input connected to the heating terminal of the oxygen probe (2).

4. A circuit as claimed in claim 1, characterised in that said circuit comprises drive switch means (18) connected between the heating the terminal (12) and the reference potential line and having a control terminal connected to a drive output (32) of the control unit (16), the drive output supplying a drive signal (PWM) having a variable duty-cycle, in order alternatively to control the opening and closing of the drive switch means (32).

5. A method for monitoring and diagnosing an oxygen probe (2), provided with a sensitive cell (3) connected between a first and a second signal terminal (6, 7) and supplying an output voltage ($V_\lambda$), and a heating member (10) connected between a battery (11) and a heating terminal (12), the oxygen probe being connected to a monitoring and diagnosis circuit (1) having an interface stage (15) and a control unit (16) comprising first and second analog-digital converter means (26, 27) connected respectively to the first and the second signal terminals (6, 7), this interface stage (15) comprising a first resistor (20) connected between a supply line (22) and the first signal terminal (6) and having a first resistance value ($R_1$), a second resistor (23) connected between the first and second signal terminals (6, 7) and having a second resistance value ($R_2$), a third resistor (24) connected between the second signal terminal (7) and a reference potential line and having a third resistance value ($R_3$), and interface switch means (21) disposed between the supply line (22) and the first resistor (20), the method comprising the stages of:

a) calculating an internal resistance value ($R_{INT}$) of of the sensitive cell (200);

b) calculating a temperature (T) of this sensitive cell as a function of this internal resistance value ($R_{INT}$) (210);

c) determining the duty-cycle of a drive signal (PWM) (220);

d) generating the drive signal (PWM) in order to drive the heating member (230);

the method being characterised in that the stage a) of calculating the internal resistance value ($R_{INT}$) comprises the stages of:

a1) carrying out a first acquisition (110) of values of a first and a second signal voltage ($V_1$, $V_2$) pesent at the first and respectively the second signal terminal (6, 7) when the interface switch means (21) are open;

a2) carrying out a second acquisition (140) of values of these first and second signal voltages ($V_1$, $V_2$) when the interface switch means (21) are closed.

6. A method as claimed in claim 5, characterised in that the stage a) of calculating the internal resistance value ($R_{INT}$) comprises the stage of:

a3) calculating a test current (IT) flowing in the interface stage when the interface switch means (21) are closed.

7. A method as claimed in claim 6, characterised in that the stage a3) of calculating a test current ($I_T$) is obtained by calculating the test current ($I_T$) according to the equation $$I_T = V_{2ON}/R_3$$

in which ($V_{2ON}$) is the value of the second signal voltage ($V_2$) obtained during the second acquisition (140).

8. A method as claimed in claim 6, characterised in that the stage a3) of calculating a test current ($I_T$) is obtained by calculating a test current ($I_T$) according to the equation $$I_T = \frac{V_{CC} - V_{1ON} - V_{DS}}{R_1}$$

in which ($V_{CC}$) is a supply voltage supplied by the supply line (22), ($V_{1ON}$) is the value of the first signal voltage ($V_1$) obtained during the second acquisition (140) and ($V_{DS}$) is a voltage drop at the interface switch means (21) when they are closed.

9. A method as claimed in claim 6, characterised in that the stage a) of calculating the internal resistance value ($R_{INT}$) comprises the stages of:
 a4) calculating a first output value ($V_{\lambda 1}$) of the output voltage ($V_\lambda$) when the interface switch means (21) are open;
 a5) calculating a second output value ($V_{\lambda 2}$) of the output voltage ($V_\lambda$) when the interface switch means (21) are closed.

10. A method as claimed in claim 9, characterised in that the stage a) of calculating the internal resistance value ($R_{INT}$) is obtained by calculating this internal resistance value ($R_{INT}$) according to the equation $$R_{INT} = \frac{R_2(V_{\lambda 2} - V_{\lambda 1})}{R_2 I_T - (V_{\lambda 2} - V_{\lambda 1})}$$

11. A method as claimed in claim 6, in which the monitoring and diagnosis circuit (1) comprises drive switch means (18) connected between the heating terminal (12) and the reference potential line and comprising a control terminal connected to a drive output (32) of the control unit (16), characterised in that it comprises the stages of:
 e) signaling a malfunction if a heating voltage ($V_H$) present at the heating terminal (12) is greater than a predetermined threshold voltage and the drive switch means (18) are closed;
 f) signaling a malfunction if the heating voltage ($V_H$) is smaller than the predetermined threshold voltage and the drive switch means (18) are open.

* * * * *

UNITED STATES PATENT AND TRADEMARK OFFICE
CERTIFICATE OF CORRECTION

PATENT NO.   : 6,476,611 B2
DATED        : November 5, 2002
INVENTOR(S)  : Berti et al.

It is certified that error appears in the above-identified patent and that said Letters Patent is hereby corrected as shown below:

<u>Title page,</u>
Item [73], please correct the spelling of the Assignee's name to
-- Magneti Marelli S.p.A. (IT) --.

Signed and Sealed this

Third Day of June, 2003

JAMES E. ROGAN
*Director of the United States Patent and Trademark Office*